United States Patent [19]

Treybig et al.

[11] Patent Number: 4,528,391

[45] Date of Patent: Jul. 9, 1985

[54] PYRAZINO PYRAZINE COMPOUNDS AS CATALYSTS FOR PREPARING URETHANES

[75] Inventors: Duane S. Treybig; James L. Potter, both of Lake Jackson, Tex.

[73] Assignee: The Dow Chemical Company, Midland, Mich.

[21] Appl. No.: 555,761

[22] Filed: Nov. 28, 1983

[51] Int. Cl.$^3$ ............................................ C07C 125/073
[52] U.S. Cl. ...................................... 560/026; 560/16; 560/158; 521/159; 524/751
[58] Field of Search .................. 560/158, 26, 16; 521/159, 751

[56] References Cited

U.S. PATENT DOCUMENTS

| | | | |
|---|---|---|---|
| 2,345,237 | 3/1944 | Chitwood et al. | 260/268 |
| 3,759,916 | 9/1973 | Pitts et al. | 260/77.5 NC |
| 3,836,488 | 9/1974 | Pruitt et al. | 560/26 X |
| 4,353,995 | 10/1982 | Szabat et al. | 560/26 X |

Primary Examiner—Bernard Helfin
Attorney, Agent, or Firm—G. C. Cohn

[57] ABSTRACT

The reaction between a hydroxyl-containing material and an isocyanate-containing material is catalyzed by a pyrazino pyrazine compound such as 1,4,5,8-tetramethyldecahydropyrazino(2,3-b)pyrazine.

10 Claims, No Drawings

PYRAZINO PYRAZINE COMPOUNDS AS CATALYSTS FOR PREPARING URETHANES

BACKGROUND OF THE INVENTION

The present invention concerns the catalyzation of the reaction between hydroxyl-containing materials and isocyanate-containing materials with a pyrazino pyrazine compound.

The reaction between hydroxyl-containing compounds and isocyanate-containing compounds is very useful particularly in the formation of urethane products. The reaction usually requires the presence of a catalyst and in some instances it is desirable to employ a delayed action catalyst for the reaction. The catalyst employed in the present invention provides such a delay.

SUMMARY OF THE INVENTION

The present invention pertains to a process for preparing urethanes which comprises reacting a material or mixture of materials containing at least one hydroxyl group per molecule with at least one material containing at least one isocyanate or isothiocyanate group per molecule in the presence of a catalytic quantity of a pyrazino pyrazine compound represented by the formula

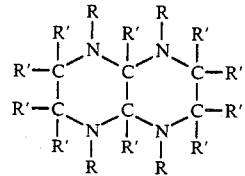

wherein each R is independently an alkyl group having from 1 to about 10, preferably from about 1 to about 4 carbon atoms and each R' is independently hydrogen or an alkyl group having from about 1 to about 10, preferably from 1 to about 4 carbon atoms.

DETAILED DESCRIPTION OF THE INVENTION

The pyrazine catalysts of the present invention can be prepared by reacting glyoxal or a substituted glyoxal with a suitable diamine as disclosed by Chitwood and McNamee in U.S. Pat. No. 2,345,237 which is incorporated herein by reference.

Suitable glyoxal compounds include those represented by the formula

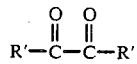

wherein each R' is independently hydrogen or an alkyl group having from 1 to about 10, preferably from 1 to about 4 carbon atoms. Particularly suitable such compounds include, for example, glyoxal, pyruvic aldehyde, 2,3-butanedione, 2,3-pentanedione, mixtures thereof and the like.

Suitable diamine compounds which can be employed to prepared the pyrazine catalysts employed in the present invention include those represented by the formula

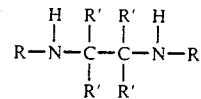

wherein each R is independently an alkyl group having from 1 to about 10, preferably from 1 to about 4 carbon atoms and each R' is independently hydrogen or an alkyl group having from 1 to about 10, preferably 1 to about 4 carbon atoms. Particularly suitable diamines include, for example, N,N'-dimethylethylenediamine, N,N'-diethylethylenediamine, N,N'-dipropylethylenediamine, N,N'-dibutylethylenediamine, N,N'-dimethyl-1,2-diaminopropane, N,N'-diethyl-1,2-diaminopropane, N,N'-dipropyl-1,2-diaminopropane, mixtures thereof and the like.

Any material containing a hydroxyl group can be employed as the hydroxyl-containing material herein; however, alcohols and polyether and polyester polyols are preferred.

Any material having at least one isocyanate group preferably those containing an average of more than one isocyanate group can be employed herein.

Also suitable are the corresponding polyisothiocyanates.

Particularly suitable polyether polyols, polyester polyols and polyisocyanates are described in *Polyurethanes, Chemistry and Technology part II. Technology*, Saunders and Frisch, Interscience, 1964 which is incorporated herein by reference.

Preferred as the active hydrogen-containing material is a polyether polyol. The preferred isocyanate-containing material is an aromatic polyisocyanate.

The quantity of catalyst which can be suitably employed in the present invention depends upon the particular reactants and catalyst employed; however an amount of from about 0.0001 to about 10, preferably from about 0.001 to about 5 parts by weight of catalyst per 100 parts by weight of the hydroxyl-containing material is usually sufficient.

Likewise the temperature employed in conducting the reaction between the hydroxyl-containing material and the isocyanate-containing material likewise depends upon the particular reactants and catalyst employed. However, usually the temperature employed is from about $-10°$ C. to about 300° C., preferably from about 0° C. to about 100° C. is employed. It is also pointed out that it is well known that the reaction between a hydroxyl group and an isocyanate group is exothermic. The time employed is that which is necessary to complete the reaction or sufficiently complete the reaction for practical purposes such as in the case of molded articles to provide sufficient green strength such that the article can be removed from the mold whereupon completion of the reaction can be obtained by subjecting the article to higher temperature for an additional period of time so as to develop optimum properties.

The following examples are illustrative of the invention but are not to be construed as to limiting the scope thereof in any manner.

EXAMPLE 1

(Preparation of 1,4,5,8-tetramethyldecahydropyrazino(2,3-b)pyrazine)

A 30 wt.% aqueous solution of glyoxal (65.8 g, 1.14 mole) was added dropwise to a stirred chilled (1° C.)

70% methanolic solution of sym-dimethylethylenediamine (400 g, 4.54 mole) in a nitrogen atmosphere. The rate of addition of the aqueous-solution of glyoxal was controlled so that all the solution was added after an hour (3600 s) with a maximum rise in temperature of 28° C. The reactor contents were a yellow colored liquid. Water and methanol were removed by rotary evaporation at 100° C. A red viscous liquid was removed by using a separatory funnel. Electron impact gas chromatography-mass spectrometry indicated the molecular weight of the yellow colored liquid was 198. Infrared spectrometry showed the absence of amide and hydroxyl groups. The proton ('H) and carbon 13 ($^{13}C$) nuclear magnetic resonance spectra for the mixture of cis- and trans-1,4,5,8-tetramethyldecahydropyrazino-(2,3,-b)-pyrazine was consistent with that obtained by Ferguson et al, *J. Chem. Soc.*, Perkin Trans 2, 1976, 13, 1564. More than 25 g of the mixture of cis- and trans-1,4,5,8-tetramethyldecahydropyrazino(2,3-b)pyrazino was soluble in 100 ml of dipropylene glycol or tetrahydrofuran.

absorption and respective recording time of the isocyanate absorption are recorded in Table I for no catalyst, 91.4% mixture of cis- and trans-1,4,5,8-tetramethyldecahydropyrazino(2,3-b)pyrazine (TMDPP), triethylenediamine (TEDA) and N,N'-dimethylpiperazine (DMP). A plot of these values indicates that the TMDPP catalyzed the diphenylmethane-4,4'-diisocyanate and triethylene glycol reaction after a 2½ (150 s) minute delay. TEDA and DMP catalyzed the diphenylmethane-4,4'-diisocyanate and triethylene glycol reaction with no delay.

The peak height of the isocyanate absorption and respective recording time of the isocyanate absorption was entered into a least square program to determine the rate constant for the three catalysts. The rate constant (K) and the ratio of the rate constant of the catalyst to the rate constant of no catalyst (K/Ko) are summarized in Table II.

TABLE I

THE LOGARITHM OF THE PEAK HEIGHT OF THE ISOCYANATE ABSORPTION (ln NCO) AND RESPECTIVE RECORDING TIME (SECONDS) FOR NO CATALYST AND DIFFERENT CATALYSTS

| No catalyst | | TMDHPP | | TEDA | | DMP | |
|---|---|---|---|---|---|---|---|
| Seconds | ln NCO | Seconds | ln NCO | Seconds | ln NCO | Seconds | ln NCO |
| 619 | −0.56 | 85 | −0.45 | 95 | −0.80 | 139 | −0.50 |
| 818 | −0.58 | 238 | −0.51 | 254 | −1.56 | 261 | −0.59 |
| 914 | −0.60 | 301 | −0.56 | 314 | −1.83 | 332 | −0.65 |
| 1113 | −0.60 | 448 | −0.76 | 371 | −2.04 | 547 | −0.86 |
| 1514 | −0.69 | 618 | −1.02 | 477 | −2.21 | 758 | −1.04 |
| 1637 | −0.72 | 750 | −1.27 | 597 | −2.53 | 961 | −1.20 |
| 2213 | −0.97 | 907 | −1.56 | 654 | −2.81 | 1162 | −1.41 |
| 2262 | −0.99 | 1188 | −1.97 | — | — | 1314 | −1.54 |
| 2721 | −1.31 | — | — | — | — | 1568 | −1.74 |
| 2777 | −1.39 | — | — | — | — | — | — |
| 2911 | −1.49 | — | — | — | — | — | — |

EXAMPLE 2

The pyrazino pyrazine compound prepared in Example 1 and other known urethane catalysts, triethylenediamine and N,N'-dimethylpiperazine were employed as catalysts in the following reaction.

Each catalyst (0.50 g) was dissolved in tetrahydrofuran (50 ml). The tetrahydrofuran solution containing the catalyst (10 ml), propylene carbonate (1 ml), triethylene glycol (5.3 g) and tetrahydrofuran (150 ml) were mixed in a 250 ml erlenmeyer flask using a magnetic stirrer. Diphenylmethane-4,4'-diisocyanate (1 ml) was added to the solution containing catalyst, propylene carbonate, triethylene glycol and tetrahydrofuran. A timer was started simultaneously. The solution was then stirred vigorously for five seconds and an aliquot removed and injected into a thin (0.2 mm) infrared liquid cell. The cell was quickly capped and placed in an I.R. spectrometer capable of repetitive scanning and a scan obtained from 2500–2200 $cm^{-1}$. Next, the 800–720 $cm^{-1}$ region was scanned to obtain the propylene carbonate peak (780 $cm^{-1}$). Approximately six more scans of the 2500–2000 $cm^{-1}$ region was taken periodically with time being recorded each instant the maximum absorbance of the isocyanate band (2270 $cm^{-1}$) was observed. The scans were obtained at times such that decreases in the isocyanate absorbance was easily observed, but the scans were not acquired at regular intervals. After the final isocyanate scan was obtained, the propylene carbonate band was recorded once more. The logarithm of the peak height of the isocyanate

TABLE II

| CATALYST | K × $10^{-4}$ | K/K° |
|---|---|---|
| No catalyst | −4.00 | 1.0 |
| TMDPP | −14.7 | 3.68 |
| TEDA | −32.2 | 8.05 |
| DMP | −8.68 | 2.17 |

We claim:

1. A process for preparing urethanes or thiourethanes which comprises reacting at least one material containing at least one hydroxyl group per molecule with at least one material containing at least one isocyanate or isothiocyanate group per molecule in the presence of a catalytic quantity of a pyrazino pyrazine compound represented by the formula

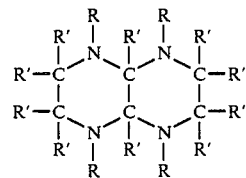

wherein each R is independently an alkyl group having from 1 to about 10, carbon atoms and each R' is independently hydrogen or an alkyl group having from about 1 to about 10, carbon atoms, wherein said reaction is conducted at a temperature of about 0°–100° C. and said reaction is delayed.

2. A process of claim 1 wherein each R is independently an alkyl group having from 1 to about 4 carbon atoms and each R' is independently hydrogen or an alkyl group having from 1 to about 4 carbon atoms.

3. A process of claim 2 wherein said pyrazino pyrazine is cis-1,4,5,8-tetramethyldecahydropyrazino-(2,3-b)pyrazine, trans-1,4,5,8-tetramethylenedecahydropyrazino(2,3,-b)pyrazine, or mixture of any two or more of such compounds.

4. A process of claim 1, 2 or 3 wherein said hydroxyl-containing material has an average of more than one hydroxyl group per molecule and said isocyanate-containing material has an average of more than one isocyanate group per molecule.

5. A process of claim 4 wherein said hydroxyl-containing material is a polyether polyol and said isocyanate-containing material is an aromatic isocyanate.

6. A process of claim 1, 2 or 3 wherein said pyrazino pyrazine is employed in quantities of from about 0.0001 to about 10 parts by weight per 100 parts by weight of hydroxyl-containing material.

7. A process of claim 6 wherein said pyrazino pyrazine compound is employed in a quantity of from 0.001 to about 5 parts by weight per 100 parts by weight of hydroxyl-containing material.

8. A process of claim 4 wherein said pyrazino pyrazine is employed in quantities of from about 0.0001 to about 10 parts by weight per 100 parts by weight of hydroxyl-containing material.

9. A process of claim 8 wherein said pyrazino pyrazine compound is employed in a quantity of from 0.001 to about 5 parts by weight per 100 parts by weight of hydroxyl-containing material.

10. A process of claim 3 wherein said pyrazino pyrazine compound is employed in a quantity of from about 0.001 to about 5 parts by weight per 100 parts by weight of hydroxyl-containing material, the isocyanate-containing material comprises diphenylmethane-4,4'-diisocyanate and the active hydrogen-containing material comprises triethylene glycol.

* * * * *